Figure 1:
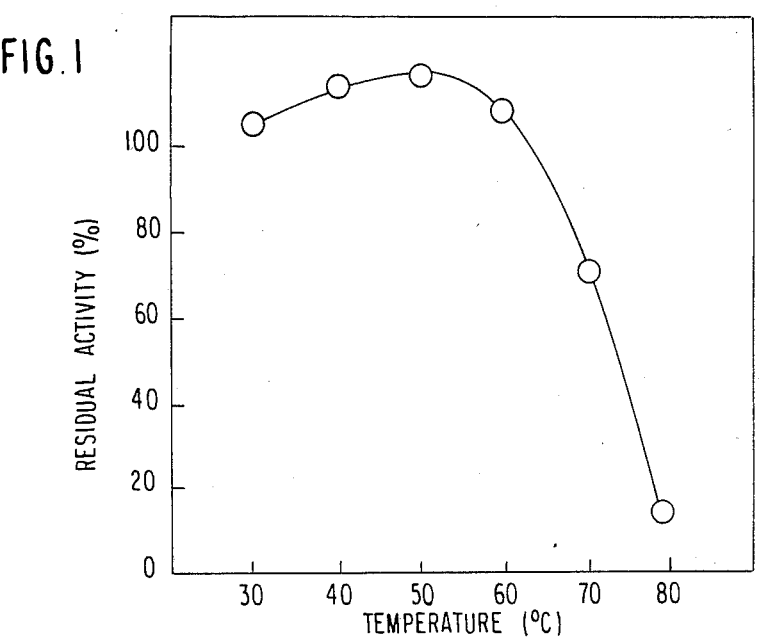
Figure 2:
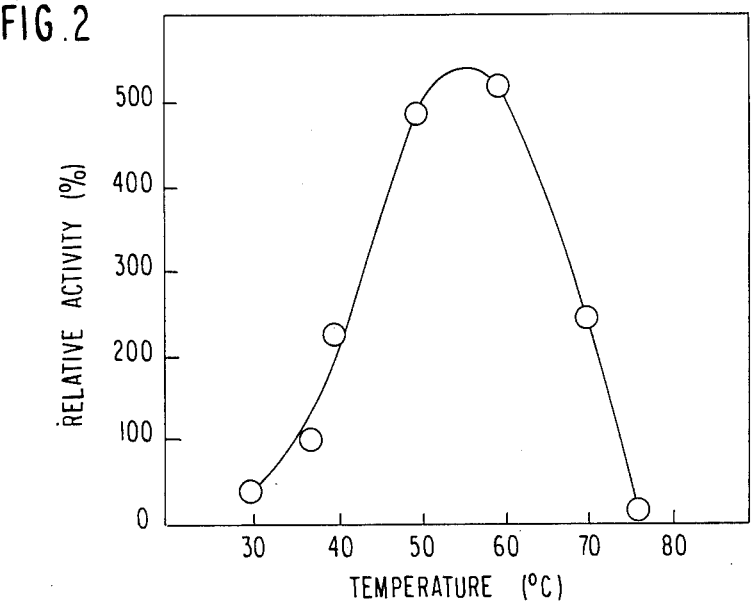
Figure 3:
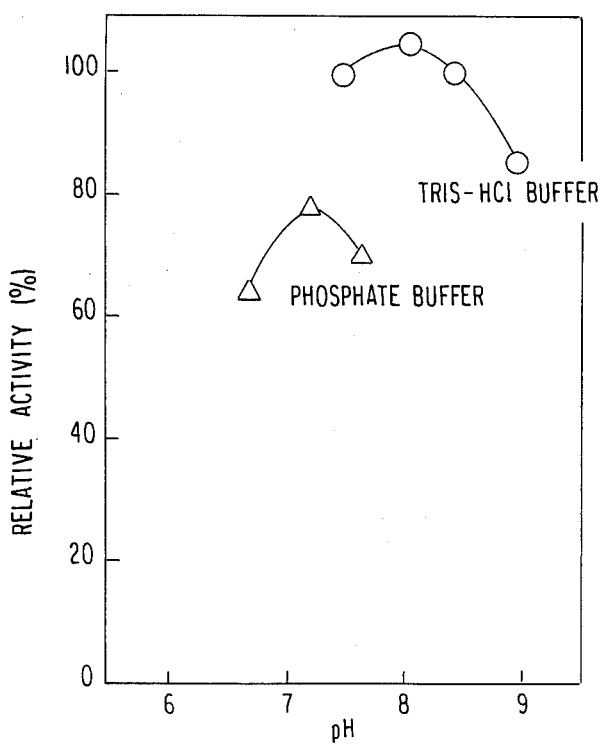
Figure 4:
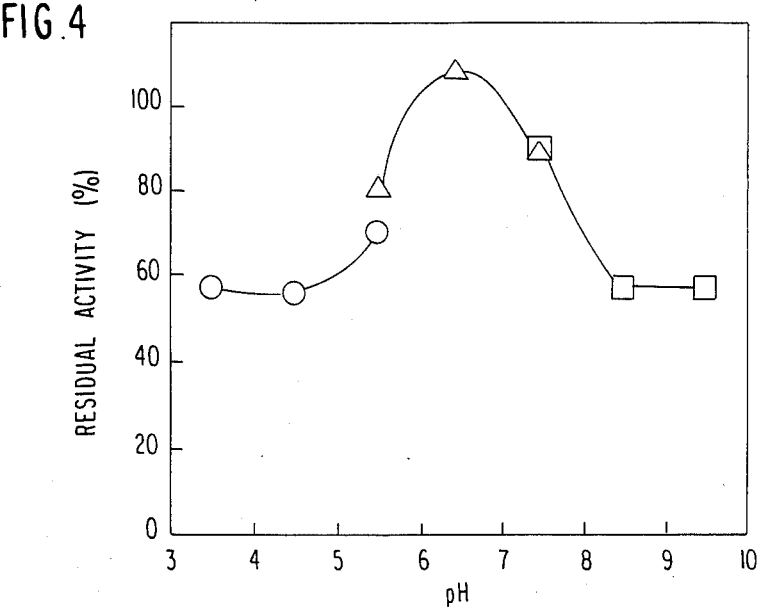
Figure 5:
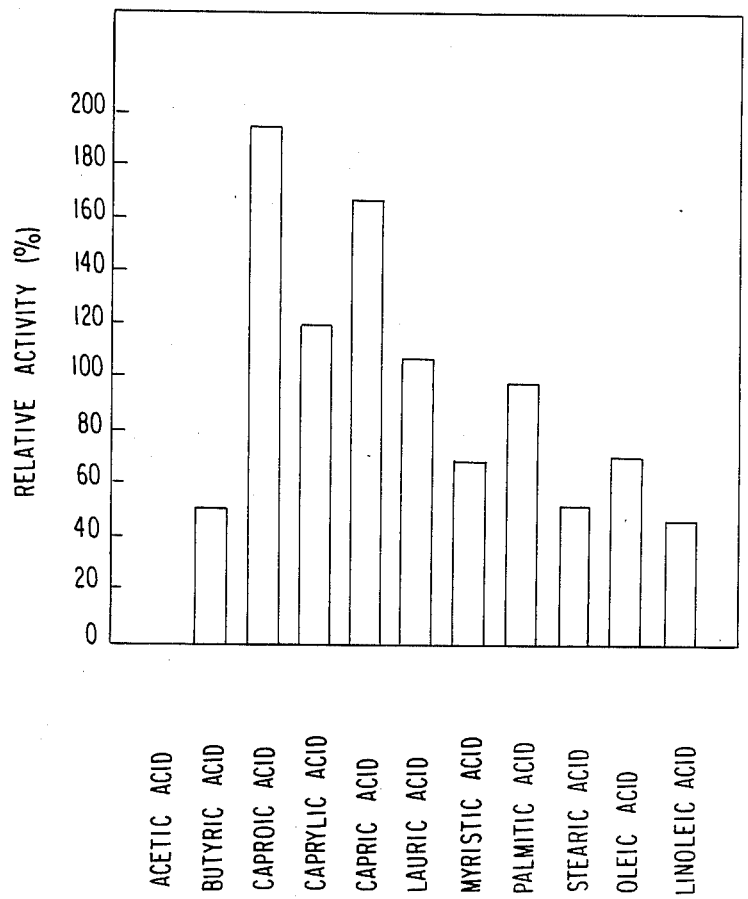

ACYL-CoA SYNTHETASE

BACKGROUND OF THE INVENTION

The present invention relates to a novel acyl coenzyme A (acyl-CoA) synthetase and thermophilic Pseudomonas UKSW-3733 strain which is capable of producing said acyl-CoA synthetase.

Acyl-CoA synthetase (hereinafter referred to as ACS) is an enzyme which activates a fatty acid into its CoA derivative (acyl-CoA) in the presence of coenzyme A (hereinafter referred to as CoA) and adenosine triphosphate (hereinafter referred to as ATP). This reaction can be represented as follows:

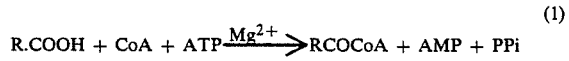

(1)

(in which R.COOH represents a fatty acid; RCOCoA represents a CoA derivative of a fatty acid (acyl-CoA); and PPi represents pyrophosphoric acid.)

It is important from medical point of view to measure the amount of free fatty acids contained in blood since it increases to a considerable degree in the case, e.g., of diabetes. The measurement is therefore recognized as an important item in clinical diagnostic chemistry. Although various chemical methods have already been known, enzymatic methods have been generally employed for the measurement in recent years because of their accuracy and convenience. In enzymatic methods, ACS is allowed to react with free fatty acids to generate acyl-CoA, AMP, PPi, etc. in accordance with the reaction formula (1) described above, and the thus formed acyl-CoA, AMP, PPi, etc., are determined by use of other enzymes. Because of their accuracy and convenience, such enzymatic methods are now mainly used instead of the chemical methods in the measurement of free fatty acid. In search of sources, in nature, of ACS to be used in the first stage of the enzymatic methods, extensive investigations have been made, and it has been found that ACS is produced by the liver microsome of rat and by various microorganisms. Some of known ACS isolated from microorganisms are already on the market (as described, e.g., *Biochemical Catalogue* of Toyobo Co., Ltd. (November, 1985) and *Enzyme Catalogue* of Toyo Jozo Co., Ltd. (June, 1982)). In particular, the distribution of microorganisms capable of producing ACS has been extensively researched, since it is possible to culture microorganisms in quantities larger than in the case of animal cells and, hence, they can be a less expensive source of the enzyme. As a result, ACS has been discovered in various microorganisms, including, e.g., bacteria, such as *Escherichia coli* (*European Journal of Biochem.*, Vol. 12, pp. 576–582, 1970), *Bacillus megaterium* strain M (*Biochemistry*, Vol. 4, pp. 85–95, 1965), and Pseudomonas 22 (*Journal of Bacteriology*, Vol. 105, pp. 1216–1218, 1971); yeasts, such as Torulopsis Y-8 (*Joural of Bacteriology*, Vol. 104, pp. 1397–1398, 1970); and actinomycetes, such as *Norcadia asteroides* (*Journal of Bacteriology*, Vol. 114, pp. 249–256, 1973). In Japanese Patent Publication No. 46757/81 is described a method for producing a highly active acyl-CoA synthetase from various microorganisms, including bacteria, yeasts, and molds, for example, *Pseudomonas aeruginosa* (IFO-3919), *Pseudomonas synxantha* (IFO-3906), *Pseudomonas schuylkilliensis* (IFO-12055), *Candida lipolytica* (IFO-0717), *Gibberella fujikuroi* (IFO-6604), *Fusarium oxysporum* (IFO-5942), *Seratia marcescens* (IFO-3054), and *Aeromonas hydrophila* (IFO-3820).

On the other hand, thermophilic bacteria belonging to the genus Pseudomonas that are incapable of producing ACS are also known *Pseudomonas thermoamylolyticus* (Japanese Patent Application (OPI) No. 106786/76), *Pseudomonas thermophila* K-2 (*Izv. Akad. Nauk. SSSR, Ser. Biol.*, Vol. 2, pp. 271–283, 1982), and *Pseudomonas hydrogenothermophila* TH-1 (*Agr. Biol. Chem.*, Vol. 41, pp. 685–690, 1977). The first is a thermophilic Pseudomonas bacterium capable of producing amylase and having an optimum temperature for growth in the range of from 60° to 65° C. The second and the third are hydrogen bacteria capable of growth on carbonate as the sole carbon source but having an optimum temperature for growth at around 50° C.

The above-described microorganisms which grow at ordinary temperatures (e.g., 20° to 37° C.) produce ACSs having only a poor storage stability, and such ACSs are liable to deactivation during purification. In addition, when such an ACS is used in a composition for measuring free fatty acids, the resulting composition may become unstable within one day because of inactivation of the ACS, or inaccurate measurement results may result because of impurities contained therein. The microorganisms are also disadvantageous in that their fermentation must be carried out at ordinary temperature, and, hence, are liable to be contaminated with various germs. This can be a serious bottleneck in large scale production of ACS.

On the other hand, none of the above-described Pseudomonas bacteria having their optimum temperature for growth in the range of from 60° to 65° C. is capable of producing ACS. In addition, it is known that enzymes obtainable from highly thermophilic bacteria having an extremely high optimum temperature for growth (65° to 80° C.) are generally impractical in spite of the fact that they have excellent storage stability. This is because their optimum reaction temperature is high, and, hence, their activity markedly decreases at temperatures of from 30° to 37° C., at which clinical diagnosis is typically performed. Upon fermentation of the above-described Pseudomonas bacteria having their optimum temperature for growth at around 50° C., hydrogen, oxygen, and carbon dioxide must be supplied to the medium at a ratio of 7/1/1 in order to maintain their growth, as they are hydrogen bacteria utilizing carbonate as the only source for their growth. Commercial fermentation of such bacteria is difficult since it cannot be controlled easily, and tends to be accompanied by the danger of explosion because of the use of hydrogen. In addition, none of the hydrogen bacteria have been known to have the ability of producing ACS.

SUMMARY OF THE INVENTION

An object of the present invention is to provide an acyl-CoA synthetase which not only possesses good storage stability, but which also exhibits a sufficient activity at temperatures of from 30° to 37° C. at which clinical diagnosis is typically performed. Another object of the invention is to provide a moderately thermophilic bacterium, Pseudomonas UKSW-3733 strain, which is capable of producing such an acyl-CoA synthetase.

In order to achieve the above objectives, the inventors have conducted extensive investigations, and, as a 10 minutes. Its activity was then determined by measuring its absorbance change at 550 nm.

The amount of enzyme that forms 1 μmol of palmitoyl CoA in 1 minute under the above conditions was designated as "1 unit."

(b) Measurement of stability:

ACS was added to 50 mM phosphate buffer (having a pH of 7.5 and containing 2 mM of ethylenediamine tetraacetate and 4 mM of 2-mercaptoethanol) to give an ACS solution containing 0.45 mg/ml of ACS.

The resulting ACS solution as incubated for 15 minutes each at temperatures varying from 30° to 80° C. with a step of 5° to 10° C., and the residual activity of the ACS was measured in accordance with the method described in paragraph (a) above.

(c) Measurement of optimum temperature

Reaction Solution (I) shown in paragraph (a) above was incubated at a temperature varying from 30 to 80° C. with a step of 10° C. To this was then added ACS, and the reaction was allowed to proceed exactly for 10 minutes at the same temperature.

In order to determine palmitoyl CoA formed, Reaction Solution (II) was added thereto and allowed to react at 37° C. for 10 minutes. The activity of the enzyme was then determined by measuring its absorbance change at 550 nm.

(d) Measurement of optimum pH:

The activity of ACS was measured in a similar manner as in paragraph (a) above, except that 0.2 M phosphate buffer (pH 6.5 to 7.5) and 0.2 M Tris-HCl buffer (pH 7.5 to 9.0) were used in place of the buffer of Reaction Solution (I).

(e) Measurement of stable pH range:

ACS was added to an acetate buffer (pH 3.5 to 5.5), a phosphate buffer (pH 5.5 to 7.5) or a Tris-HCl buffer (pH 7.5 to 9.5) to make 0.14 mg/ml ACS solutions. The solutions were allowed to stand for 20 hours at 25° C., and then the residual activity of ACS was determined in accordance with the method described in paragraph (a) above.

(f) Measurement of substrate specificity:

The ACS activity was determined in a similar manner as in paragraph (a) above, except that various fatty acids were used in place of palmitic acid employed in Reaction Solution (I) shown in paragraph (a) above.

(9) Purification of enzyme:

The enzyme of the present invention can be purified, e.g., according to the method described below.

At first, 80 g of wet cells are suspended into 0.1 M phosphate buffer (pH 7.5) and then disrupted by ultrasonic treatment. To the resulting dispersion is added protamine sulfate up to a concentration of 0.2% by weight, and precipitates formed (e.g., nucleic acids) are removed by centrifugation. The thus obtained crude enzyme solution is adsorbed on a column of DEAE cellulose and developed by means of linear gradient elution of KCl. ACS active fractions are combined, and the combined solution is desalted and then adsorbed on a column of Matlex Blue A (a product of Pharmacia Japan Co., Ltd.) and developed by means of linear gradient elution of KCl. The ACS fractions obtained are added up to 15% saturated concentration of ammonium sulfate, adsorbed by a column of phenyl cephallose and then developed by means of reverse gradient elution of water and ammonium sulfate, to provide a purified sample of ACS.

In order to obtain the ACS according to the present invention, thermophilic microorganisms capable of growing at a temperature of 45° C. or more are cultured, and the ACS produced is then extracted therefrom. Any thermophilic microorganisms capable of producing the ACS according to the invention can be employed. A specific example of such microorganism is a biologically pure culture of Pseudomonas UKSW-3733, which has been deposited at the Fermentation Research Institute, the Agency of Industrial Science and Technology, Ministry of International Trade and Industry, Japan, under Deposition Number FERM P-8550 (conformity with the International Assession Number BP-1263 under Budapest Treaty). This is a novel strain separated from the soil at the hot spring of Atagawa in Higashiizu-cho, Kamo-gun, Shizuoka prefecture, Japan, by a screening of Koch's plate culture (for example, see William Burrows, *Textbook of Microbiology*, 19th ed., p. 21, W.B. Saunders Company, U.S.A.) using oleic acid as a carbon source.

Any conventional medium can be used for the culturing of the strain. A liquid medium can be particularly preferable. As nutrient sources for such a medium, there can be used organic acids, alcohols, etc., which can be assimilated by the strain. As nitrogen sources for the strain, there can be used organic substances for the strain, such as amino acids, peptone, meat extracts, and yeast extracts, as well as inorganic nitrogen-containing compounds, such as ammonium sulfate and ammonium nitrate. In addition, there can be used inorganic salts, for example, salts of potassium, sodium, phosphoric acid, zinc, iron, magnesium, manganese, copper, calcium, and cobalt; as well as salts of trace metals, corn steep liquor, vitamins, nucleic acids, or the like. The UKSW-3733 strain can be cultured under aerobic conditions for 8 hours at a temperature in the range of from 35° to 60° C., preferably from 45° to 55° C., by employing any of the above-described media. The strain can be cultured either by a batch method or by a continuous method.

In the present invention, the isolation and purification of the ACS can be carried out, e.g., in accordance with the method described in paragraph (9) above (purification of enzyme), or in accordance with the following method: Cells are suspended in a buffer solution and disrupted by a conventional method. The resulting suspension is extracted with a solution containing salts, surface active agents, etc., to remove nucleic acids, and then fractionated by salting-out by use of annonium sulfate, followed by column chromatography by use of various stationary phases. As examples of column chromatography applicable for its purification, mention may be made of ion exchange chromatography employing, e.g., diethylaminoethyl (DEAE) cellulose; hydrophobic chromatography employing, e.g., phenylagarose; gel chromatography; and affinity chromatography. Highly pure ACS can be obtained in accordance with the methods described hereinabove.

Microbiological characteristics of the Pseudomonas UKSW-3733 strain are as described hereinbelow.

In the examination of microbiological characteristics of the strain, there were utilized the processes and media described by Takeharu Hasegawa (editor and author), *Classification and Identification of Microorganisms*, published by Tokyo University Shuppankai; and Riichi Sakazaki, *Baichigaku Kakuron*, published by Naya Shoten. Hydrogen and carbonate assimilating properties of the strain were investigated in accordance with the procedures described in *Agr. Biol. Chem.*, Vol. 41, pp. 685–690, 1977.

Morphological observations (Cultured for 1-2 days at 50° C.)
1. Cell size: 1.5–2.0×0.7–0.8 (μm), bacilliform
2. Polymorphism: None
3. Motility: yes
4. Spore: None
5. Flagellum: Single polar flagellum
6. Gram stain: Negative
7. Acid-fast staining: None State of growth (Cultured for 1-2 days at 50° C.)
1. Broth agar plate culture:
   Shape: Circular
   Margin: Smooth
   Elevation: None (flat)
   Gloss: None
   Surface: Smooth
   Color: Semitransparent
2. Broth agar slant culture:
   Degree of growth: Medium
   Shape: Grows uniformly along inoculation line
3. Broth liquid culture:
   Turbidity: Slightly turbid
   Precipitate: Formed in small quantity
   Coloration & decoloration: None
   Change in pH of medium: Alkali was formed
4. Broth agar stab culture:
   Shape: Linear
   Surface growth: Good
   Depth growth: None
5. Broth gelatin stab culture:
   (After being cultured at 50° C. for an appropriate period of time with addition of 20% by weight of gelatin and then chilled, the solidified state of the culture was observed.)
   Liquefaction: None
6. Litmus milk:
   Formation of acids or alkalis: None
   Liquefaction & solidification: None Physiological properties (Cultured for 1-2 days at 50° C.)
1. Reduction of nitrate: Observed
2. Denitrification reaction: Positive
3. MR test: Negative
4. VP test: Negative
5. Formation of indole: None
6. Formation of hydrogen sulfide; None
7. Hydrolysis of starch: None
8. Utilization of citric acid: None
9. Utilization of nitrates: None
10. Utilization of ammonium salts: Observed (+)
11. Formation of dye: None
12. Urease activity: None
13. Oxidase activity: Observed (+)
14. Catalase activity: Observed (+)
15. Growth pH: 5.0 to 9.0
    Optimum pH for growth: 6.0 to 7.0
16. Growth temperature: 35° to 60° C.
    Optimum growth temperature: 45° to 55° C.
17. Behavior toward oxygen: Aerobic
18. OF test:
    Glucose: Not degraded
    Ethanol: Oxidized
19. Arginine dihydrolase activity: None
20. Accumulation of polyhydroxybutyric acids: None
21. Formation of acetic acid from ethanol at pH 4.5: None
22. Requirement of nutrinents: None
23. Utilization of hydrogen and carbonates: None Formation of acids and gases from carbon sources (Observed for one week at 50° C.)

|  | Acids | Gases |
|---|---|---|
| 1. L-arabinose | — | — |
| 2. D-xylose | — | — |
| 3. D-mannose | — | — |
| 4. D-fructose | — | — |
| 5. D-glucose | — | — |
| 6. D-galactose | — | — |
| 7. Maltose | — | — |
| 8. Sucrose | — | — |
| 9. Lactose | — | — |
| 10. Trehalose | — | — |
| 11. D-sorbitol | — | — |
| 12. D-mannitol | — | — |
| 13. Inositol | — | — |
| 14. Glycerol | — | — |
| 15. Starch | — | — |

Assimilability of carbon sources
(Observed for 1 week at 50° C.)
1. Growable on the following carbon sources: Acetic acid, succinic acid, propionic acid, butyric acid, caproic acid, myristic acid, oleic acid, ethanol, propanol, and butanol
2. Weakly growable on the following carbon sources: Fructose and ethylene glycol
3. Not growable on the following carbon sources: Xylose, maltose, sucrose, mannitol, geraniol, L-arginine, L-histidine, glucose, starch, L-valine, β-hydroxybutyric acid, citric acid, β-alanine, and carbonic acid Based on the above microbiological characteristics, the identity of the strain was investigated in accordance with the methods described in *Bergey's Manual of Determinative Bacteriology,* 8th ed. and *Bergey's Manual of Systematic Bacterilology,* Vol. 1. As a result, it was determined that the strain belongs to the genus Pseudomonas. Characteristics of the strain resemble most closely *Pseudomonas pseudoalcaligenes.* However, these two strains markedly differ in their optimum temperatures for growth. Namely, according to *Manual of Systematic Bacteriology,* Vol. 1, the optimum temperature for growth of *P. pseudoalkaligenes* is 35° C., whereas it is in the range as high as from 45° to 55° C. in the case of the strain according to the present invention. In addition, there is also a difference in assimilability of carbon sources, that is, *P. pseudoalcaligenes* is capable of assimilating both β-hydroxybutyric acid and L-arginine, whereas the strain according to the invention lacks the ability of assimilating the two compounds.

As described hereinbefore, the following thermophilic bacteria belonging to the genus Pseudomonas are known to the art: *Pseudomonas thermoamylolyticus* (Japanese Patent Application (OPI) No. 106786/76); *P. thermophila* K-2 (*Izv. Akad. Nauk. SSSR, Ser. Biol.,* Vol. 2, pp. 271–283, 1982); and *P. hydrogenothermophila* TH-1 (*Arg. Biol. Chem.,* Vol. 41, pp. 685–690, 1977). However, the first strain is not known to have an ability of producing ACS. In addition, the strain has its optimum temperature for growth at a temperature in the range of from 60° to 65° C., forms acids from various sugars, and possesses the ability to liquefy gelatin. The microbiological properties of the strain are therefore clearly different from those of the strain according to the present invention. The other two strains, *P. thermophila* K-2 and *P. hydrogenothermophila* TH-1, are also not known to have the ability of producing ACS. In addition, they are hydrogen bacteria which are capable of growth on carbonate as the sole carbon source, whereas the strain according to the present invention has the ability of producing ACS and is incapable of growth on carbonate when used as the sole carbon source. Therefore, the strain according to the present invention is apparently different from the known strains.

As described hereinabove, the optimum temperature for growth and other characteristics of the strain according to the present invention are apparently different from those of any of the hitherto known strains. It was therefore judged to be a new strain and named Pseudomonas UKSW-3733. The strain was deposited at the Fermentation Research Institute, the Agency of Industrial Science and Technology, Ministry of International Trade and Industry, Japan, under the Deposit Number FERM P-8550, as described hereinabove.

The present invention will further be illustrated by way of examples. In the examples, percentages are based on weight unless otherwise specified.

EXAMPLE 1 AND COMPARATIVE EXAMPLES 1-2

In 500 ml Erlenmeyer flasks was placed 100 ml each of a medium (pH 7.0) composed of 0.2% of sodium oleate, 0.03% of yeast extract, 0.1% of $(NH_4)_2SO_4$, 0.1% of $KH_2PO_4$, 0.1% of $Na_2PHO_4.12H_2O$, 0.05% of $MgSO_4.7H_2O$, and 0.2 ml/l of Triton X-100, and the medium was sterilized under a wet heat at 121° C. at a pressure of 1 atm. Pseudomonas UKSW-3733 (FERM P-8550) strain grown on a broth agar slant medium was inoculated in 10 of the 500 ml Erlenmeyer flasks and cultured at 50° C. with rotary shaking. The cultured solutions thus obtained (1,000 ml) were inoculated in a 30 l jar fermentor (Type MSJ-U provided with a flat vane turbine, made by Marubishi Rika Sochi Co., Ltd.) containing 20 l of medium which had the same composition as above (the medium employed had been sterilized beforehand under a wet heat at 121° C. for 10 minutes at a pressure of 1 atm). The strain was cultivated at 50° C. with aeration (20 l per minute) and agitation (400 r.p.m.). The strain started to grow immediately after the commencement of the cultivation. As the pH of the culture medium decreased with the propagation of the strain, 4N NaOH was added thereto during the course of the cultivation, so as to maintain its pH at from 6.8 to 7.2. It reached a stationary state in about 8 hours, and almost all the oleic acid contained in the medium was consumed. The cultured product was subjected to centrifugation to give about 80 g of wet cells.

The thus obtained wet cells 80 g) was suspended in 700 ml of a 0.1 M phosphate buffer (pH 7.5) and disrupted by ultrasonic treatment (200 W, 10 minutes). The fragments of the cells were removed by centrifugation (8,000 G, 20 minutes) to provide a crude enzyme solution.

To the crude enzyme solution was added 0.2% of protamine to remove nucleic acids, and the supernatant was applied to a column (4.4 cm (diameter)×30 cm (length)) packed with DEAE cellulose and subjected to linear gradient elution of 0.6 M KCl. ACS was eluted at a concentration of KCl of from 0.1 to 0.2 M.

The ACS fraction obtained was desalted by means of dialysis and then applied to a column (2.4 cm (diameter)×10 cm (length)) packed with Matrex Blue-A (a product of Pharmacia Co., Ltd.), and then subjected to linear gradient elution of 0.6 M KCl. ACS was eluted at a concentration of KCl of from 0.05 to 0.1 M.

The thus obtained ACS fraction was added up to 15% saturated concentration of ammonium sulfate and applied to a column (1.1 cm (diameter)×10 cm (length)) packed with Phenylsephalose and subjected to gradient elution of 10% saturated concentration of ammonium sulfate solution and distilled water (the concentration of ammonium sulfate was lowered gradually). ACS was eluted when the concentration of ammonium sulfate was reduced almost to zero.

The thus obtained ACS showed an almost single band in electrophoresis and had a specific activity of 0.42 units/mg protein. The physical and chemical characteristics of the thus purified enzyme were identical with those described hereinbefore.

The stability of the thus obtained ACS sample was investigated in the following manner.

Figure 6:
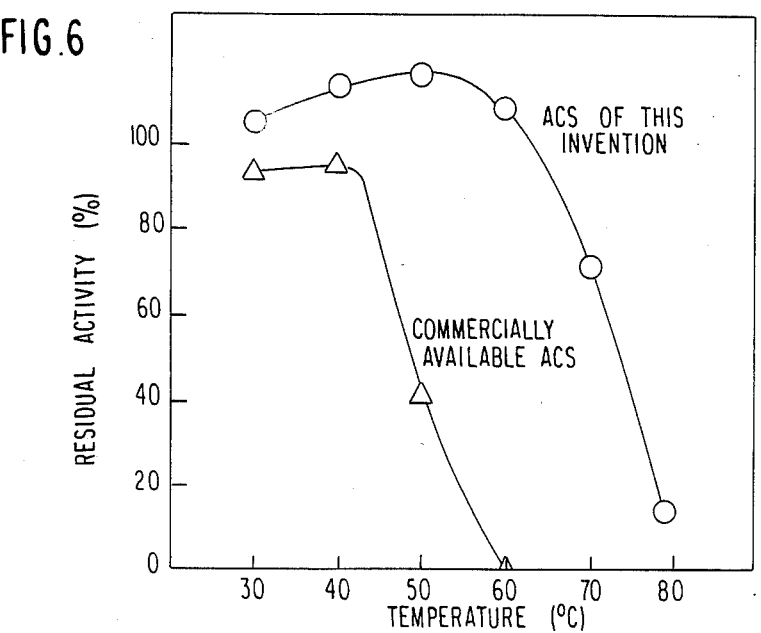

The purified ACS sample was diluted with a 50 mM phosphate buffer (pH 7.5 and containing 2 mM of ethylenediaminetetraacetate and 4 mM of 2-mercaptoethanol), so as to form a 0.90 mg/ml solution of ACS. The ACS solution was incubated, for 15 minutes each, at temperatures ranging from 30° to 80° C. with a step of from 5° to 10° C., and the residual activity of the ACS was determined. The activity of the ACS remained 100% at 55° to 60° C., that is to say, no reduction in its activity was observed at the temperatures. After incubation at 70° C., there was observed a reduction of about 30% in the activity of the ACS (see FIG. 6).

For the purpose of comparison, a commercially available ACS obtained from a Pseudomonas bacterium having its optimum temperatures for growth at ordinary temperature (about 37° C.) was treated in the same manner as above. Only 40% of its activity remained after 15 minutes of incubation at 50° C. It showed no activity at all after being incubated for 15 minutes at 60° C. (see FIG. 6).

The above results clearly show that the ACS of the present invention is dramatically more stable against heat than ACS available on the market.

The long-term storage stability of the ACS was compared with that of the commercially available ACS derived from microorganism which grow at ordinary temperature in the following manner.

The purified ACS sample obtained above (or the ACS according to the invention) and the commercially available ACS were separately diluted with a 50 mM phosphate buffer (pH 7.5 and containing 2 mM of EDTA and 4 mM of 2-mercaptoethanol) in such a manner that the ACSs are contained in a concentration of 0.45 mg/ml or 0.48 mg/ml, respectively. The solutions were incubated in a water bath at 37° C., and the changes in their residual activity were measured along with the lapse of time.

Figure 7:
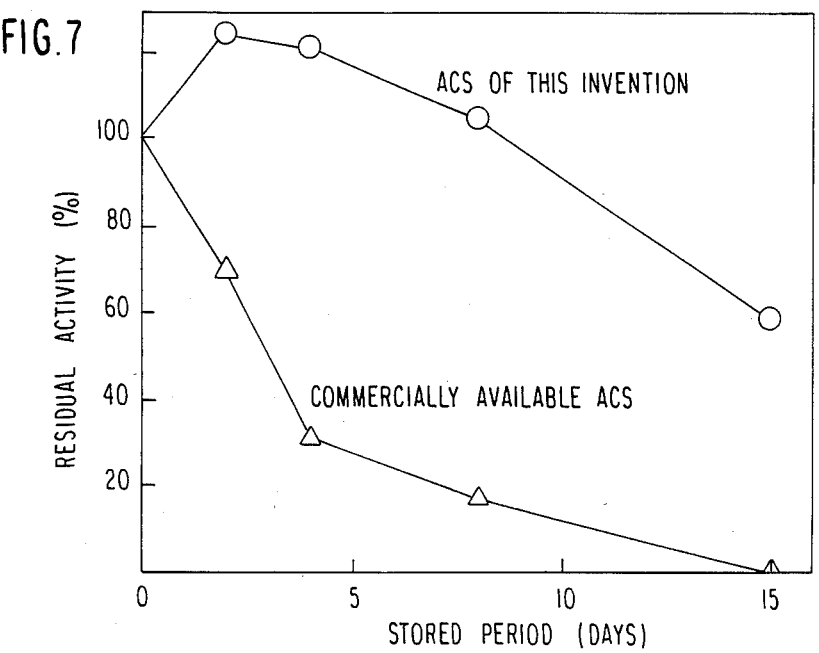

As is shown in FIG. 7, the residual activity of the commercially available ACS was only about 30% after 4 days of incubation, whereas the activity of the ACS of the invention remained at about 60% after 15 days of incubation.

It would therefore be clear that the ACS of the present invention is far superior in its storage stability to the commercially available ACS.

REFERENCE EXAMPLE 1

A measurement of free fatty acids contained in a serum of a male adult was performed at 37° C. by using a commercially available free fatty acid determination kit composed of Coloring Compositions A and B (NEFA C-Test, a product of Wako Pure Chemicals Co., Ltd.). A change of absorbance of 0.112 resulted at 550 nm. A solution having a composition equivalent to the above Composition A was prepared by using the ACS obtained in Example 1, and the above measurement was repeated by using the solution in combination with Coloring Composition B. A change of absorbance of 0.115 was obtained at 550 nm, which corresponds to a fatty acid concentration of 510 μEq/l.

The above results evidence that the reaction involving the ACS of the invention proceeds well at 37° C. and it is usable for the measurement of free fatty acids contained in human serum.

EXAMPLE 2

The UKSW-3733 strain was cultivated in a 30 l fermentor in the same manner as in Example 1. The cultivation proceeded well and reached an almost stationary phase in about 8 hours. When the density of the carbon source (oleic acid) contained in the medium was lowered to less than 0.005%, a continuous cultivation was started. During the continuous cultivation, the medium was supplied to the tank at a rate of 9 l/hour and the fermented broth was drawn out at the same rate by using metering pumps. That is, the dilution (D) was carried out at a cultivation rate of 0.45 hr$^{-1}$, which was decided by taking into consideration the maximum specific growth rate ($\mu$max) of the strain in the above batch cultivation.

The continuous cultivation continued stably, thereby producing wet cells at a rate of 2.25 g/l/hr. After 10 hours, 450 g of wet cells were obtained and the cultivation was stopped.

The thus obtained wet cells contained 1,200 units/kg of ACS. The ACS was purified and its characteristics were examined in the same manner as in Example 1. The ACS, it was confirmed, had the stable and excellent characteristics identical with those of the ACS obtained in Example 1.

While the invention has been described in detail and with reference to specific embodiments thereof, it will be apparent to one skilled in the art that various changes and modifications can be made therein without departing from the spirit and scope thereof.

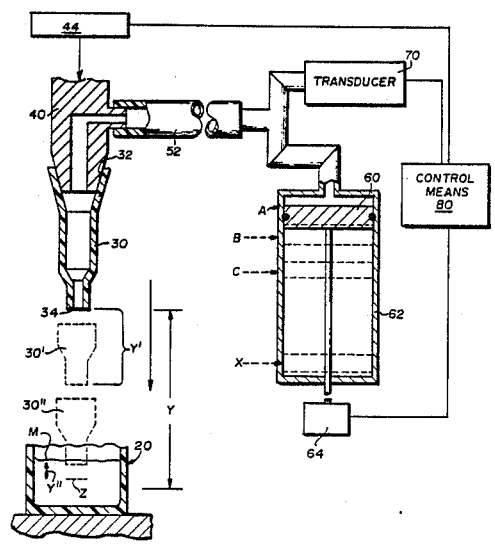

What is claimed is:

1. An acyl-CoA synthetase having the following characteristics:

(a) Reaction:
  Capable of acting on saturated or unsaturated lower to higher fatty acids to produce a CoA derivative thereof (Acyl-CoA), adenosine monophosphate, and pyrophosphoric acid, in the presence of adenosine triphosphate and coenzyme A;

(b) Stability:
  Having a residual activity of not less than about 50% after being incubated in a buffer (pH about 7.5) for about 15 minutes at a temperature of about 55° C.; and (c) Optimum reaction temperature:
  Having an optimum reaction temperature between 50° and 60° C.

2. A synthetase as in claim 1, wherein said synthetase is a product produced by a thermophilic micoorganism having an optimum temperature for growth in the range of from 45° to 55° C.

3. A biologically pure culture of Pseudomonas UKSW-3733 capable of producing acyl-CoA synthetase in recoverable amounts, which has an optimum growth temperature in the range of from 45° to 55° C. and is incapable of assimilating carbonates.

4. A synthetase as in claim 1, wherein the synthetase has its highest activity at a pH of from about 7.0 to 8.5, and retains not less than 50% of its activity after being treated at a pH of 3.5 or at a pH of 9.5 for 20 hours at 25° C.

5. A synthetase as in claim 1, wherein the synthetase is entirely deactivated by mercuric chloride, is slightly inhibited by zinc chloride and ferric sulfate, and is not substantially affected by sodium chloride, potassium chloride, and calcium chloride.

6. A synthetase as defined in claim 4, wherein said synthetase is a product produced by a thermophilic micoorganism having its optimum temperature for growth in the range of from 45° to 55° C.

7. A synthetase as defined in claim 5, wherein said synthetase is a product produced by a thermophilic micoorganism having its optimum temperature for growth in the range of from 45° to 55° C.

8. A synthetase as in claim 1, wherein the synthetase is obtained from Pseudomonas UKSW-3733.

9. A synthetase as in claim 1, wherein the synthetase has the essential characteristics of a synthetase obtained from Pseudomonas UKSW-3733.

* * * * *

United States Patent [19]

Jessop et al.

[11] Patent Number: 4,794,085

[45] Date of Patent: Dec. 27, 1988

[54] APPARATUS AND METHOD FOR DETECTING LIQUID PENETRATION BY A CONTAINER USED FOR ASPIRATING AND DISPENSING THE LIQUID

[75] Inventors: Thomas C. Jessop, Webster; Raymond L. Nelson; Rodney J. Whitcomb, both of Rochester, all of N.Y.

[73] Assignee: Eastman Kodak Company, Rochester, N.Y.

[21] Appl. No.: 80,146

[22] Filed: Jul. 29, 1987

Related U.S. Application Data

[63] Continuation of Ser. No. 632,516, Jul. 19, 1984, abandoned.

[51] Int. Cl.⁴ .............................................. G01N 35/00
[52] U.S. Cl. .................................. 436/54; 73/863.01; 422/63; 422/64; 422/65; 422/67; 422/100; 436/49; 436/180
[58] Field of Search .................. 73/863.01, 864.24; 137/386; 141/94, 95, 250; 318/685, 592–594; 364/182; 422/63–67, 73, 100; 436/49, 54, 180

[56] References Cited

U.S. PATENT DOCUMENTS

| | | | |
|---|---|---|---|
| 3,754,444 | 8/1973 | Ure et al. .......................... | 73/863.01 |
| 3,894,438 | 7/1975 | Ginsberg ............................ | 73/863.01 |
| 3,992,158 | 11/1976 | Przybylowicz et al. ............. | 422/57 |
| 4,041,995 | 8/1977 | Columbus ........................... | 141/275 |
| 4,053,381 | 10/1977 | Hamblen et al. ................... | 204/195 M |
| 4,258,001 | 3/1981 | Pierce et al. ....................... | 422/56 |
| 4,287,155 | 9/1981 | Tersteeg et al. ................... | 422/64 |
| 4,340,390 | 7/1982 | Collins et al. ..................... | 422/64 |

FOREIGN PATENT DOCUMENTS

| | | | |
|---|---|---|---|
| 56-164957 | 12/1981 | Japan ................................. | 422/100 |
| 56-164958 | 12/1981 | Japan ................................. | 422/100 |
| 59-52759 | 3/1984 | Japan . | |

Primary Examiner—Michael S. Marcus
Attorney, Agent, or Firm—Dana M. Schmidt

[57] ABSTRACT

Apparatus and a method are described which permit the detection of penetration of liquid by an apertured container used for aspirating and dispensing the liquid. The apparatus and method feature control means for advancing the container an increment of the maximum possible distance to the liquid; generating a pressure differential within the dispensing container that is sufficient to generate a signal that is indicative of whether the container aperture is closed by the liquid; detecting and signalling the pressure produced within the container by such a pressure differential; and comparing such signalled pressure against a reference value determinative of whether the container has penetrated the liquid.

18 Claims, 4 Drawing Sheets